US00PP24489P3

(12) United States Plant Patent
Caster et al.

(10) Patent No.: US PP24,489 P3
(45) Date of Patent: May 27, 2014

(54) BLUEBERRY PLANT NAMED 'DRISBLUEFIVE'

(50) Latin Name: ***Vaccinium corymbosum* L.**
Varietal Denomination: DrisBlueFive

(75) Inventors: Brian K. Caster, Salinas, CA (US); Jennifer K. Izzo, Watsonville, CA (US); Arlen Draper, Payson, AZ (US); Paul M. Lyrene, Micanopy, FL (US)

(73) Assignees: Driscoll Strawberry Associates, Inc., Watsonville, CA (US); Florida Foundation Seed Producers, Inc., Marianna, FL (US)

( * ) Notice: Subject to any disclaimer, the term of this patent is extended or adjusted under 35 U.S.C. 154(b) by 85 days.

(21) Appl. No.: 13/573,335

(22) Filed: Sep. 11, 2012

(65) Prior Publication Data
US 2014/0075616 P1 Mar. 13, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

*Primary Examiner* — Annette Para
(74) *Attorney, Agent, or Firm* — Jondle Plant Sciences division of Swanson & Bratschun, L.L.C.

(57) ABSTRACT

A new and distinct variety of blueberry plant named 'DrisBlueFive' particularly distinguished by having a very low chilling requirement, early harvest season with medium to high productivity, and firm, sweet berries with aromatic flavor, is disclosed.

2 Drawing Sheets

Genus and species: *Vaccinium corymbosum* L.
Variety denomination: 'DrisBlueFive'.

BACKGROUND OF THE NEW PLANT

The invention relates to a new and distinct blueberry variety designated 'DrisBlueFive' and botanically known as *Vaccinium corymbosum* L. This new blueberry variety was discovered in Santa Cruz, Calif. in June 1999 and originated from a cross between the proprietary female parent blueberry plant 'FL 97-16' (unpatented) and the proprietary male parent blueberry plant 'Windsor' (U.S. Plant Pat. No. 12,783). The original seedling of the new variety was first asexually propagated at a nursery in Monterey, Calif. 'DrisBlueFive' was subsequently asexually propagated and underwent further testing at a nursery in Santa Cruz, Calif. for thirteen years. The present invention has been found to be stable and reproduce true to type through successive asexual propagations via softwood cuttings.

Plant Breeder's Rights for this variety have not been applied for. 'DrisBlueFive' has not been made publicly available or sold more than one year prior to the filing date of this application.

SUMMARY OF THE INVENTION

The following are the most outstanding and distinguishing characteristics of this new cultivar when grown under normal horticultural practices in Santa Cruz, Calif.

1. A very low chilling requirement;
2. Early harvest season with medium to high productivity; and
3. Firm, sweet berries with aromatic flavor.

DESCRIPTION OF THE PHOTOGRAPHS

This new blueberry plant is illustrated by the accompanying photographs which show fruit of the plant as well as the flowers and leaves. The colors shown are as true as can be reasonably obtained by conventional photographic procedures. The photographs are of plants that are 13 years old.

DESCRIPTION OF THE NEW CULTIVAR

Figure 1:
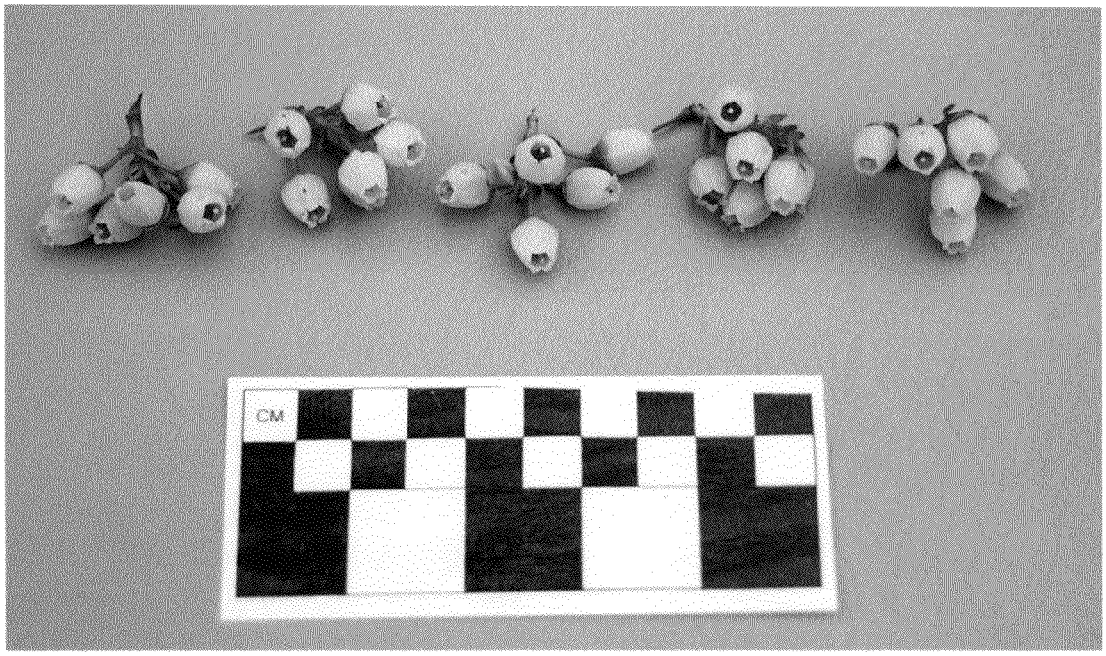
FIG. 1 shows a close-up of the mature flowers.
Figure 2:
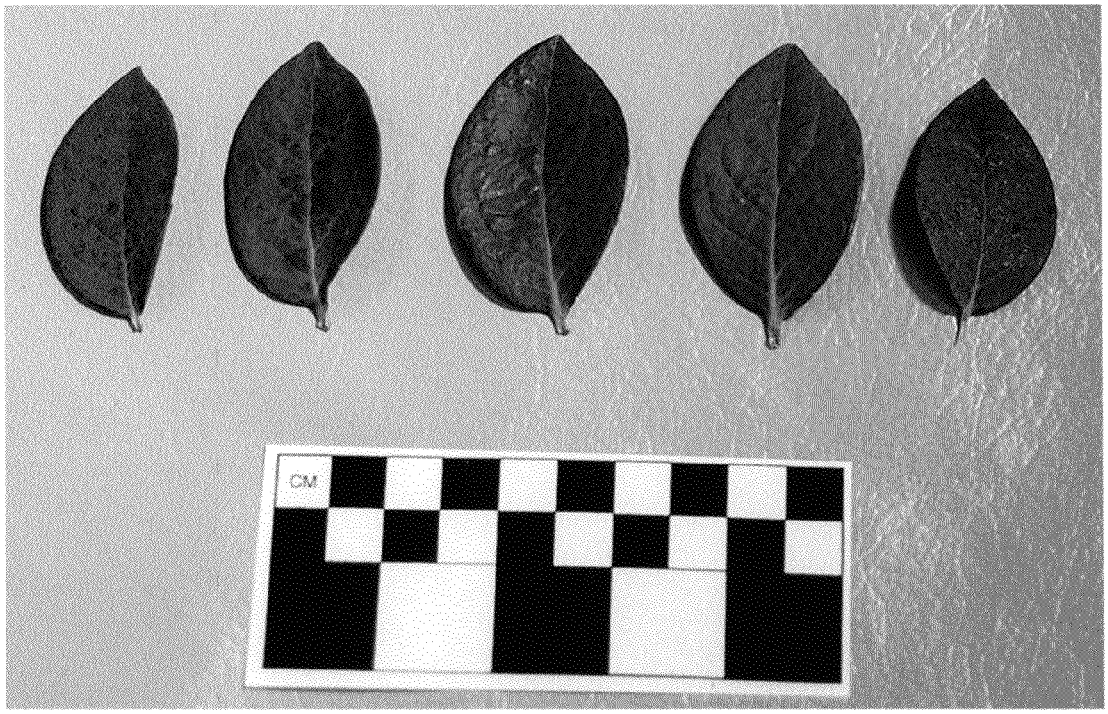
FIG. 2 shows a close-up of the leaves.
Figure 3:
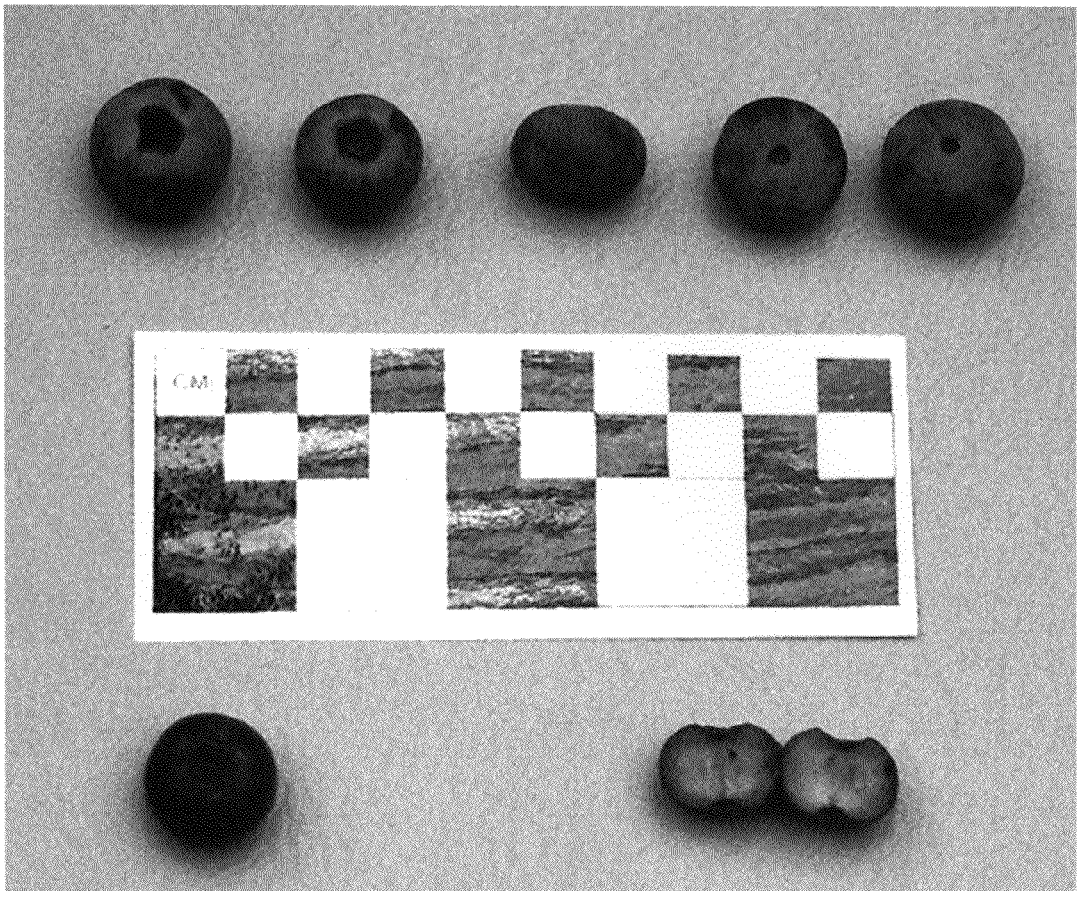
FIG. 3 shows a close-up of the whole fruit and a cross-section of the fruit.

The following detailed description sets forth the distinctive characteristics of 'DrisBlueFive.' The data which define these characteristics is based on observations taken in Santa Cruz, Calif. from 1999 to 2012. This description is in accordance with UPOV terminology. Color designations, color descriptions, and other phenotypical descriptions may deviate from the stated values and descriptions depending upon variation in environmental, seasonal, climatic and cultural conditions. 'DrisBlueFive' has not been observed under all possible environmental conditions. The botanical description of 'DrisBlueFive' was taken from 13 year-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION

Classification:

*Family.*—Ericaceae.
*Botanical.*—*Vaccinium corymbosum* L.
*Common name.*—Blueberry.
*Variety name.*—'DrisBlueFive'.

Parentage:

*Female parent.*—The proprietary blueberry plant 'FL 97-16' (unpatented).

*Male parent.*—The proprietary blueberry plant 'Windsor' (U.S. Plant Pat. No. 12,783).

Plant:

*Size.*—Medium.

*Height.*—126.2 cm.

*Width.*—157.2 cm.

*Length/width ratio.*—0.8.

*Plant vigor.*—Strong.

*Growth habit.*—Semi-erect.

*Productivity.*—Medium to high.

*Cold hardiness.*—Medium.

*Chilling requirement.*—Very low; 150-250 chilling hours.

*Propagation.*—Soft wood cuttings.

*Time of vegetative bud burst.*—Early to medium.

*Fruiting type.*—Only on one-year-old shoots.

*Cane renewal.*—Strong.

*Internode length* (*upper half on one-year old shoot*).—33.8 mm.

*One-year old canes* (*young canes*).—Length: 107.0 cm. Diameter at the base: 9.0 mm. Diameter at the tip: 5.0 mm. Texture: Smooth. Color (One-year old shoot, branch and canes): RHS 144C (Medium yellow-green).

*Five-year old canes* (*mature canes*).—Length: 132.0 cm. Diameter at the base: 17.0 mm. Diameter at the tip: 3.8 mm. Texture: Rough. Color: RHS N200B (Medium brown).

Leaves:

*Length.*—Medium; 4.84 cm.

*Width.*—Medium; 2.97 cm.

*Length/width ratio.*—1.6; longer than broad.

*Shape.*—Elliptic.

*Apex.*—Acute.

*Base.*—Cuneate.

*Margin.*—Entire.

*Glossiness.*—Medium.

*Pubescence.*—Glabrous (Absent).

*Sheath.*—Absent.

*Arrangement.*—Alternate.

*Venation.*—Reticulate.

*Color.*—Upper surface: Dark; RHS 189A (Dark greyed-green). Lower surface: Medium; RHS 191A (Medium greyed-green).

*Appearance of leaf bud.*—Early.

*Internode length* (*one-year old shoot, upper half*).—Medium; 17.58 mm.

Petiole:

*Length.*—2.5 mm.

*Diameter.*—1.71 mm.

*Color.*—RHS N145B (Light yellow-green).

Flowers:

*Length* (*excluding peduncle*).—Long; 9.88 mm.

*Diameter.*—8.08 mm.

*Length/width ratio.*—1.2.

*Color.*—RHS 155C (White).

*Flower bud.*—Length: 8.7 mm. Width: 3.3 mm. Number of flowers per bud: 7. Color on mature buds: RHS 65C (Light red-purple) and RHS 155B (White).

*Petal width.*—4.74 mm.

*Fragrance.*—Very faint or absent.

*Time of beginning flowering on one-year shoot.*—Early.

*Time of flowering* (50% *full bloom*).—Early; March 6.

*Pedicel.*—Length: 8.51 mm. Diameter: 1.09 mm. Color: RHS 145B (Medium yellow-green).

*Corolla.*—Aperture diameter: 2.62 mm. Shape: Urceolate. Size of corolla tube: Medium. Corolla tube color: Very weak or absent; RHS N155C (White). Ridges on tube: Absent.

*Peduncle length.*—3.49 cm.

Reproductive organs:

*Style length* (*including stigma*).—Medium; 6.51 mm.

*Style color.*—RHS 144B (Medium yellow-green).

*Ovary color.*—RHS 189B (Medium greyed-green).

*Pollen amount.*—Medium to high.

*Pollen color.*—RHS 9D (Light yellow).

*Anther color.*—RHS 164A (Medium greyed-orange).

Fruit:

*Size.*—Medium to large.

*Length.*—12.46 mm.

*Width.*—17.09 mm.

*Length/width ratio.*—0.7.

*Fruit pedicel diameter.*—1.23 mm.

*Weight.*—1.8 g.

*Number of berries per cluster.*—9.

*Cluster density.*—Medium.

*Shape in longitudinal sections.*—Oblate.

*Intensity of green color* (*immature fruit with bloom*).—Medium; RHS 139C (Medium green).

*Color of skin* (*immature fruit without bloom*).—RHS N77A (Dark purple).

*Color of skin* (*mature fruit without bloom*).—RHS N186A (Greyed-purple).

*Color of skin* (*mature fruit with bloom*).—RHS 107D (Light blue).

*Intensity of bloom* (*mature fruit*).—Strong to very strong.

*Attitude of sepals.*—Incurving and erect.

*Calyx.*—Diameter of basin: Large; 7.09 mm. Depth of basin: Deep; 4.44 mm. Diameter/depth ratio: 1.6.

*Flesh color.*—RHS 149C (Light yellow-green).

*Firmness.*—Firm.

*Sweetness.*—Medium.

*Acidity.*—Low.

*Time of beginning of fruit ripening* (*one-year old shoots*).—Medium.

*Harvest season.*—Early.

*Harvest interval.*—May 4 to July 5.

Seeds:

*Length.*—1.62 mm.

*Width.*—1.18 mm.

*Length/width ratio.*—1.4.

*Abundance.*—Medium to high.

*Color.*—RHS 164A (Medium greyed-orange).

Resistance to pests and diseases: Data not available.

COMPARISON WITH PARENTAL AND COMMERCIAL VARIETIES

'DrisBlueFive' differs from the male parent blueberry variety 'Windsor' (U.S. Plant Pat. No. 12,783) in that 'DrisBlueFive' has elliptic shaped leaves with an acute apex and a berry weight of 1.8 grams, whereas 'Windsor' has oval to lanceolate shaped leaves with an acuminate apex and a berry weight of 2.48 grams. Additionally, 'DrisBlueFive' has a low chilling requirement of 150 to 250 hours, whereas 'Windsor' has a higher chilling requirement of about 300 hours.

'DrisBlueFive' differs from the commercial variety 'DrisBlueOne' (U.S. Plant Pat. No. 20,449) in that 'DrisBlueFive' has leaves with an acute apex and firm berries with low acidity, whereas 'DrisBlueOne' has leaves with a broadly acute apex and very firm berries with medium acidity. Additionally, 'DrisBlueFive' has a very low chilling requirement, whereas 'DrisBlueOne' has a medium chilling requirement.

'DrisBlueFive' differs from the commercial variety 'DrisBlueTwo' (U.S. Plant Pat. No. 20,488), in that 'DrisBlueFive' has leaves with an cuneate base and an entire margin, whereas 'DrisBlueTwo' has leaves with a broadly acute base and a serrulate margin. Additionally, 'DrisBlueFive' has oblate shaped berries with low acidity, whereas 'DrisBlueTwo' has nearly spherical shaped berries with medium acidity.

We claim:

1. A new and distinct variety of blueberry plant named 'DrisBlueFive' as shown and described herein.

* * * * *